United States Patent [19]

van Staaveren

[11] Plant 5,030

[45] Apr. 12, 1983

[54] CARNATION NAMED STACHERRY

[75] Inventor: Maurits C. van Staaveren, 30 Hornweg, at 1432 GM, Aalsmeer, Netherlands

[73] Assignees: B. V. Handelskwekerij; M. C. van Staaveren, both of Aalsmeer, Netherlands

[21] Appl. No.: 225,333

[22] Filed: Jan. 15, 1981

[51] Int. Cl.[3] ..... A01H 5/00

[52] U.S. Cl. ..... Plt./71

[58] Field of Search ..... Plt./71-72

*Primary Examiner*—Robert E. Bagwill

*Attorney, Agent, or Firm*—Chas. W. Rummler

[57] ABSTRACT

A new variety of carnation plant of the spray or miniature type distinguished by the deep pink coloration of its medium sized, high centered blooms which are produced continuously on plants of about average height and which are borne singly on sturdy, long and upright peduncles.

1 Drawing Figure

BACKGROUND OF THE NEW PLANT

My new variety of carnation plant originated as a seedling derived by my crossing of carnation varieties selected from breeding stock maintained in greenhouse at Aalsmeer, The Netherlands, with the object of developing improved color and better production in time and quantity. Upon discovery of this plant, I reproduced it at Aalsmeer, The Netherlands, by cuttings, to better observe its growing characteristics and flowering property and subsequently, the new plant appearing to have commercially favorable characteristics, it was propagated through successive generations which demonstrated that its novel characteristics hold true from generation to generation and appear to be firmly fixed. Commercial propagation of this plant by cuttings is now being done in greenhouses at Aalsmeer, The Netherlands.

DESCRIPTION OF THE DRAWING

This new carnation plant is illustrated by the accompanying full color photographic drawing, which shows inflorescence of the full grown plant, the color rendition being as nearly true as it is possible to obtain by conventional photographic procedures.

DESCRIPTION OF THE NEW PLANT

The following is a detailed description of my new variety of carnation plant based upon observations of plants grown under conventional greenhouse practices, the color designations being according to The R.H.S. Colour Chart published by The Royal Horticultural Society of London, England.

THE PLANT

Origin: Seedling.

Parentage:

*Seed parent.*—No. 005-3C (unpatented).

*Pollen parent.*—Pink Barbie (unpatented). The seed parent for this variety is maintained in greenhouse at Aalsmeer, The Netherlands, and is identified in my permanent records by the above designation.

Classification:

*Botanic.*—*Dianthus caryophyllus.*

*Commercial.*—Greenhouse carnation for cut flowers.

Form: Bush.

Height: About 1.30 m.

Growth: Strong, vigorous and upright.

Branching: Normal.

Foliage:

*Quantity.*—Abundant.

*Leaf size.*—Moderate.

*Leaf shape.*—Oblong.

*Color.*—Upper side — Grey-Green with waxy layer. Under side — Grey-Green with waxy layer.

THE BUD

Size: Medium, about 20 mm. in diameter and about 40 mm. long.

Shape: Generally ovoid.

Opening rate: Moderate.

Color:

*When sepals first divide.*—Yellow Green.

*When petals begin to unfurl.*—Yellow Green.

Sepals:

*Condition.*—Upstanding.

*Color.*—Inside — Grey Green. Outside — Yellow Green with White tips.

Calyx:

*Shape.*—Cylindrical.

*Size.*—Moderate, about 20 mm. broad and about 30 mm. long.

*Splitting.*—The calyx does not split.

*Aspect.*—Smooth.

Peduncle: Rigid and erect.

*Color.*—Grey Green.

THE FLOWER

Blooming habit: Continuous and profuse.

Size of bloom: Medium.

*Diameter.*—About 60 mm.

*Depth.*—About 35 mm.

Borne: Singly.

Shape: High centered when bloom first opens. This form does not change.

Petalage:

*Number of petals.*—About 50.

*Arrangement.*—Generally imbricated.

*Color.*—Outer and inside petals — 55A-58C. Reverse side — 55A-58C.

*Texture.*—Soft.

*Appearance.*—Shiny.

Peduncle:

*Length.*—About 50 cm.

*Character.*—Sturdy and upright.

*Color.*—Dark Green.

Persistence: The petals hang on and dry and the bloom stays upright.

Fragrance: Weak.

Lasting quality:

*On the plant.*—About 14 days.

*As a cut flower.*—About 10 days.

REPRODUCTIVE ORGANS

Stamens:

*Anthers.*—Moderate in number and of varying lengths.

*Filaments.*—Color — Cream.

*Pollen.*—Color — Yellow.

Pistils:

*Number.*—Three.

*Length.*—About 40 mm.

Fruit: The fruit is fertile.

*Shape.*—Oblong.

*Color at maturity.*—Green/Brown.

I claim:

1. A new and distinct variety of carnation plant, substantially as herein shown and described, characterized by its continuous and profuse production of medium sized flowers of a deep pink color carried on long, strong and erect stems.

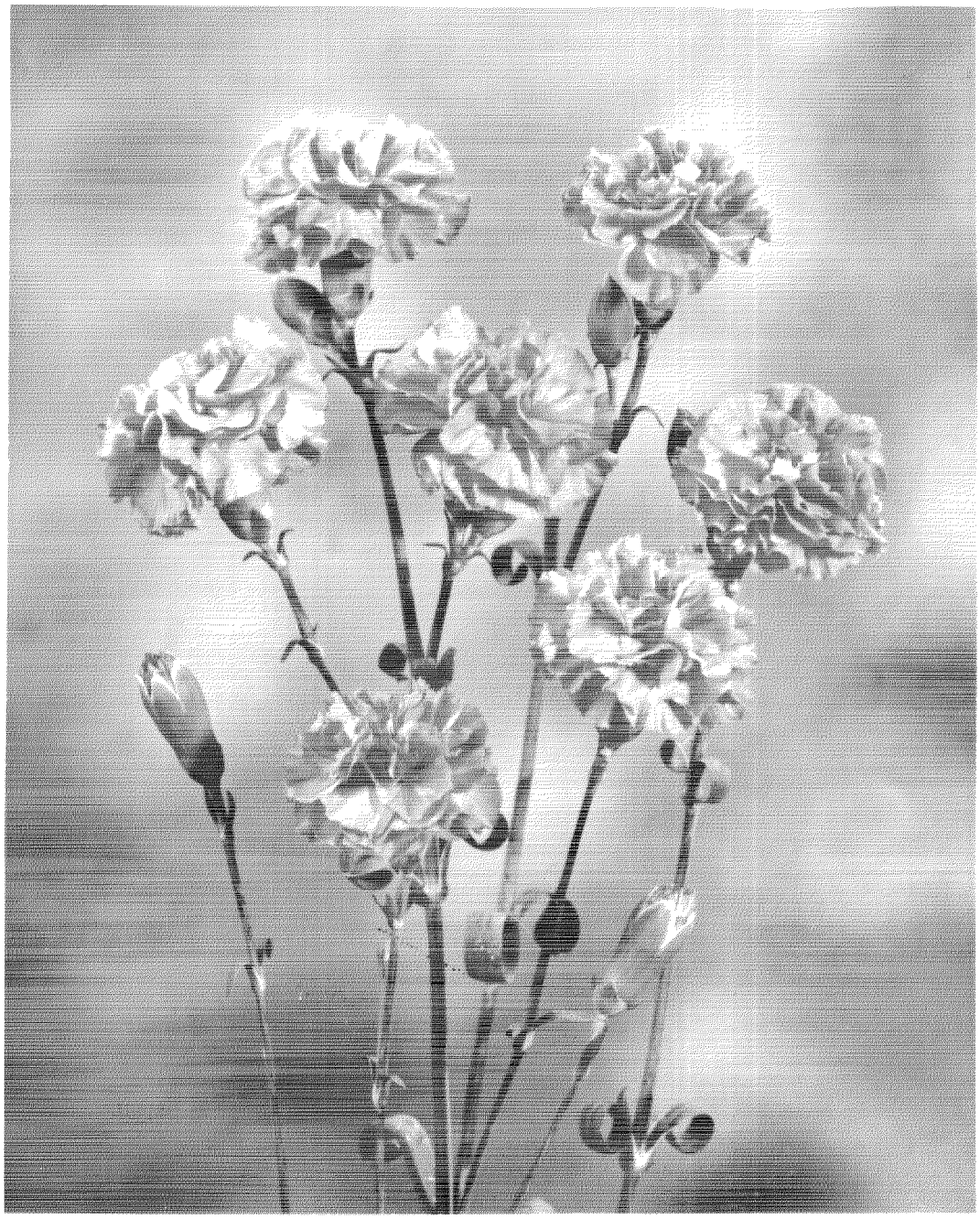

* * * * *